(12) United States Patent
Parker et al.

(10) Patent No.: US 9,066,663 B2
(45) Date of Patent: Jun. 30, 2015

(54) HEART MONITOR

(75) Inventors: Dawood Parker, Whitland (GB); Mark Bowes, Whitemill (GB)

(73) Assignee: MELYS AFS LIMITED, Whitland (GB)

( * ) Notice: Subject to any disclaimer, the term of this patent is extended or adjusted under 35 U.S.C. 154(b) by 1220 days.

(21) Appl. No.: 12/302,042

(22) PCT Filed: May 22, 2007

(86) PCT No.: PCT/GB2007/050280
§ 371 (c)(1),
(2), (4) Date: Sep. 22, 2009

(87) PCT Pub. No.: WO2007/135464
PCT Pub. Date: Nov. 29, 2007

(65) Prior Publication Data
US 2010/0022897 A1    Jan. 28, 2010

(30) Foreign Application Priority Data
May 24, 2006    (GB) .................................. 0610292.5

(51) Int. Cl.
*A61B 5/024*    (2006.01)

(52) U.S. Cl.
CPC .......... *A61B 5/02416* (2013.01); *A61B 5/02427* (2013.01)

(58) Field of Classification Search
CPC ........... A61B 5/02416; A61B 5/02427; A61B 5/0245; A61B 5/04525; A61B 5/046

USPC .................. 600/508–509, 512–515, 522–523
See application file for complete search history.

(56) References Cited

U.S. PATENT DOCUMENTS

| | | | |
|---|---|---|---|
| 5,544,661 A | | 8/1996 | Davis |
| 5,860,860 A | * | 1/1999 | Clayman .......................... 463/36 |
| 5,921,940 A | * | 7/1999 | Verrier et al. .................. 600/518 |
| 6,264,614 B1 | * | 7/2001 | Albert et al. ................... 600/528 |
| 2004/0116972 A1 | | 6/2004 | Marcovecchio |
| 2006/0122527 A1 | * | 6/2006 | Marcovecchio .............. 600/515 |
| 2007/0219453 A1 | * | 9/2007 | Kremliovsky et al. ....... 600/509 |
| 2007/0239215 A1 | * | 10/2007 | Bhunia et al. ..................... 607/6 |
| 2010/0121209 A1 | * | 5/2010 | Cazares et al. ................ 600/510 |
| 2010/0222655 A1 | * | 9/2010 | Starr et al. .................... 600/310 |

FOREIGN PATENT DOCUMENTS

| | | |
|---|---|---|
| EP | 0848965 A2 | 6/1998 |
| EP | 1300110 A2 | 4/2003 |

* cited by examiner

*Primary Examiner* — Catherine Voorhees
(74) *Attorney, Agent, or Firm* — Gordon & Jacobson, PC

(57) ABSTRACT

A heart monitor for use as a non-invasive screening tool for identifying potential atrial fibrillation in patients comprises a sensor for producing an output waveform of the patient's actual sinus rhythm, a processing unit arranged to store the normalized waveform of an ideal sinus rhythm and to compare the actual and ideal sinus rhythm waveforms and to produce an output dependant on the difference on a display. The value of the output is indicative of whether the patient is atrial fibrillation or other cardiac arrhythmia.

23 Claims, 4 Drawing Sheets

HEART MONITOR

BACKGROUND OF THE INVENTION

1. Field of the Invention

The present invention relates to a heart monitor and more particularly but not solely to a heart monitor for use as a non-invasive screening tool for identifying potential atrial fibrillation in patients.

2. Related Background Art

In a healthy person the heartbeat is tightly regulated by waves of electrical activity that cause the co-ordinated contraction of the heart muscles. Electrical impulses are generated in the sinu-atrial node in the right atrium of the heart and travel to the atrioventricular node. The pulses then travel through the Bundle of "His" and down the left and right Bundle branches, causing the ventricles to beat rhythmically.

In a person with atrial fibrillation the electrical impulses are no longer generated in the sinu-atrial node but have shifted to some other area of the heart and travel continuously around the left and right atria. This means that they arrive at the atrioventricular node unpredictably with the result that the ventricles beat but with beats which are irregularly irregular.

Chronic atrial fibrillation is the commonest arrhythmia (abnormal heart rhythm) seen in medical practice. It causes an increased morbidity and mortality and adds significantly to the burden of health care costs. The prevalence of atrial fibrillation increases with age (0.5% of those aged 50-59 years to 8.8% of those aged 80-89), as do the associated risks.

There is a six-fold increase of thromboembolic phenomena in those with atrial fibrillation. Atrial fibrillation also accounts for 33% of strokes in elderly people. In an ageing population there will be a greater incidence of stroke and, therefore, an increase in the associated social and health-care costs.

In General Practice, patients with atrial fibrillation show symptoms of breathlessness, palpitations and fatigue as a result of reduced cardiac output. Heart failure may develop. Reversal of the atrial fibrillation to sinus rhythm will alleviate the symptoms.

Once diagnosed, treatment for atrial fibrillation is low-cost and highly effective. For example, prescribing a particular kind of drug can reduce the risk of stroke in atrial fibrillation sufferers by 70%. However, atrial fibrillation cannot be diagnosed without the patient taking an electrocardiogram (ECG), which is expensive in both time and equipment. For this reason, electrocardiograms are not used for mass screening.

Patients also have complications of atrial fibrillation such as stroke or cardiac failure. In such circumstances, atrial fibrillation can be detected by pulse palpation (detecting the pulse by touch) and confirmed by electrocardiogram. It is recognised that electrocardiogram diagnosis is more accurate in terms of specificity and sensitivity than pulse palpation which is subjective.

Screening for atrial fibrillation is not practiced as a routine procedure in most countries. The obvious place to provide screening is in the community, and doctors' surgeries are well placed to carry out this role. However, electrocardiogram recordings are time-consuming and expensive and they require reporting by an appropriately trained doctor. The concept of screening for atrial fibrillation is therefore fraught with difficulties.

We have now devised a heart monitor which can be used as a non-invasive screening tool for atrial fibrillation.

SUMMARY OF THE INVENTION

In accordance with the present invention, there is provided a monitor for monitoring the heart of a patient, the monitor comprising a sensor for producing an output waveform of the patient's actual sinus rhythm, means for storing the waveform of an ideal sinus rhythm and means for comparing the actual and ideal sinus rhythm waveforms and for producing an output dependant on the difference.

In use, the output of the monitor can be used to provide an indication of an abnormal heart rhythm. The monitor can thus be used to screen patients in the community and patients with abnormal heart rhythms can be referred to an appropriately trained doctor for further investigation, who can confirm the existence or otherwise of atrial fibrillation.

In one embodiment the sensor is arranged to produce an output waveform of the patient's actual heart rhythm by sensing the electrical activity of the heart to produce an electrocardiogram. However, in a preferred embodiment, the sensor is preferably arranged to produce an output waveform of the patient's actual heart rhythm by sensing the pulsatile flow of blood through a part of the patient's body to produce a plethysmogram.

Preferably the sensor comprises a light emitter and a light detector arranged to detect a change in the transmissivity of said part of the patient's body as blood flows therethrough in a pulsatile manner.

The sensor has high sensitivity to pulse irregularities and is highly specific for detecting cardiac arrhythmia. The monitor provides an easily accessible means of screening the population for a condition that carries high morbidity and mortality. Appropriate treatment of this condition has greater efficacy (in terms of numbers needed to treat) than many other interventions (e.g. treating mild to moderate hypertension and the use of statins to lower blood cholesterol).

Preferably, the light emitter is arranged to emit light having a wavelength of 500 to 1100 nm.

Preferably said comparing means is arranged to compare the frequency spectrums of said actual and ideal sinus rhythm waveforms.

Preferably, said storing means is arranged to store a peak mathematical function representative of the frequency spectrum of said ideal sinus rhythm waveform. Preferably, the mathematical function is a Fourier transformation.

Preferably the storing means is arranged to store a model of the frequency spectrum of an ideal sinus rhythm waveform. The frequency spectrum of an ideal sinus rhythm waveform comprises a discontinuous series of saw tooth peaks at frequencies $f$, $2f$, $3f$ and with amplitudes of $1/f$, $1/2f$, $1/3f$ etc, where $f$ is the heart rate.

Preferably the peak mathematical function representative of the frequency spectrum of said ideal sinus rhythm waveform is area normalised, such that the area beneath between the frequency limits of interest is 1.

Preferably the detector is arranged to produce a patient mathematical function representative of the frequency spectrum of said actual sinus rhythm waveform. Preferably, the mathematical function is a Fourier transformation.

Preferably the patient mathematical function of the actual waveform is area normalised, such that the area beneath between the frequency limits of interest is 1.

The stored peak function of the ideal sinus rhythm waveform is preferably stored without an indication of the fundamental frequency i.e. the heart rate, since the comparable heart rate of each patient will vary. Accordingly, said comparing means is preferably arranged to determine the fundamental frequency of the actual sinus rhythm waveform and to compare the frequency spectrum of said actual sinus rhythm waveform with the frequency spectrum of an ideal sinus rhythm waveform having the same or similar fundamental frequency. In this manner the comparison of the spectra is made between the waveform at the same fundamental heart rate. Accordingly, the best match possible is made between the ideal spectrum for sinus rhythm and the actual spectrum.

Preferably the comparing means is arranged to produce a peak result by summing the products of the produced mathematical function of the actual sinus rhythm with the stored mathematical function of the ideal sinus rhythm using a range of fundamental frequencies for the stored model.

Preferably the comparing means is arranged to determine the frequency at which the peak result is maximised: The frequency value that yields the greatest product summation identifies the heart rate (fundamental component) of the patient. The magnitude of the greatest product summation can itself be used to provide an indication of whether or not the patient is suffering from atrial fibrillation. Typically, if the result is higher than 0.3, the patient is likely to have abnormal cardiac rhythm. If the result is lower than 0.2, the patient is likely to have normal cardiac rhythm.

Preferably range of fundamental frequencies extends between 0.6 and 3.3 hertz (40 to 200 heart beats per minute).

In theory the spectrum includes frequencies up to infinity but in practice the magnitude of very high frequency harmonics is small and can be neglected. Accordingly, the products are preferably summed using integrals over a range of the frequency spectrum which includes said fundamental frequency and at least one harmonic frequency.

However, in order to further improve the reliability of the peak result, the comparing means preferably introduces a trough function comprising a mathematical function representative of the inverse frequency spectrum of said ideal sinus rhythm waveform. This trough function essentially consists of a continuous series of saw tooth peaks of equal amplitude with the same peak spacing as the frequency spectrum of said ideal sinus rhythm waveform but with its peaks falling midway between those thereof. This trough function is preferably area normalised, the comparing means preferably being arranged to produce a trough result by summing the products of the produced mathematical function of the actual sinus rhythm with the trough function at the determined fundamental frequency.

Preferably the trough result is divided by the peak result to provide an index of cardiac arrhythmia.

Also in accordance with this invention, there is provided a method of examining the output waveform of a sensor arranged to monitor the heart of a patient, the method comprising comparing the output of the sensor with a stored waveform of an ideal sinus rhythm and producing an output dependant on the difference.

BRIEF DESCRIPTION OF THE DRAWINGS

An embodiment of the present invention will now be described by way of an example only and with reference to the accompanying drawings, in which.

DETAILED DESCRIPTION OF THE PREFERRED EMBODIMENT

Figure 1:
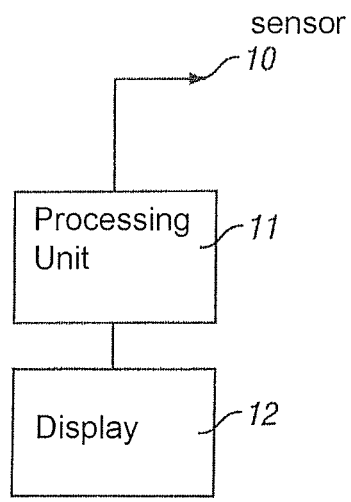
FIG. 1 is a block diagram of a heart monitor in accordance with the present invention.

Referring to FIG. 1 of the drawings, there is shown a heart monitor in accordance with the present invention, which comprises a sensor 10 for engaging a patient's finger and a processing unit 11 for receiving and interpreting the output of the sensor 10 to provide an indication on a display 12 of whether or not the patient is suffering from an abnormal heart beat (arrhythmia). The processing unit 11 and display 12 may comprise a personal computer, such as laptop, which may be connected to the sensor via an external interface circuit.

Figure 2:
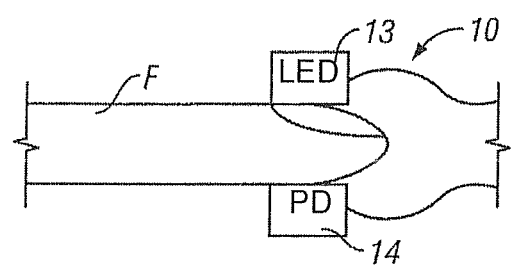
FIG. 2 is a schematic diagram of a sensor of the monitor of FIG. 1.
Figure 3:
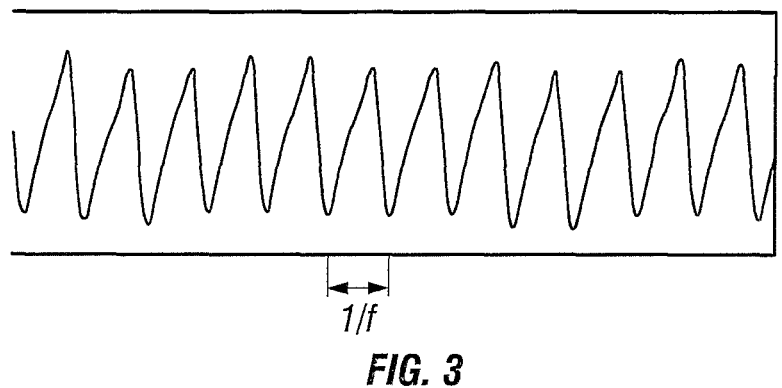
FIG. 3 is a plethysmograph of normal sinus rhythm.

Referring to FIG. 2 of the drawings, the sensor 10 comprises an LED 13 arranged to transmit light of a wavelength in the range 500 to 1100 nm through the tip of the patient's finger F. The transmitted light is collected by a photodetector 14 and the plethysmograph output thereby is fed to the processing unit Referring to FIG. 3 of the drawings, for a patient with normal cardiac function (sinus rhythm) the plethysmograph obtained in seen to be periodic. Fourier analysis teaches that such a periodic waveform is made up of the sum of a number of sinusoidal waveforms each of a different frequency. Each such frequency is an integer multiple of the frequency being approximated.

Figure 4:
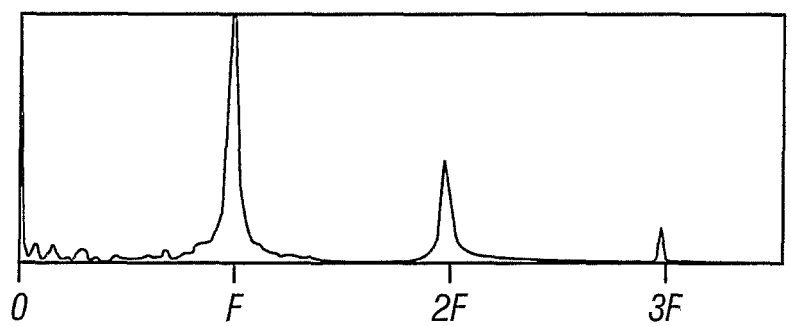
FIG. 4 is the frequency spectrum derived by Fourier analysis for the sinus rhythm of FIG. 3.

Referring to FIG. 4 of the drawings, the spectrum so derived consists of a zero frequency component 0, a fundamental frequency f equal to the heart rate of the patient and a series of harmonics at frequencies 2f, 3f etc and with amplitudes of 1/f, 1/2f, 1/3f etc. In theory the spectrum includes frequencies up to infinity but in practice the magnitude of very high frequency harmonics is small and can be neglected.

Figure 5:
FIG. 5 is a plethysmograph of sinus arrhythmia.
Figure 6:
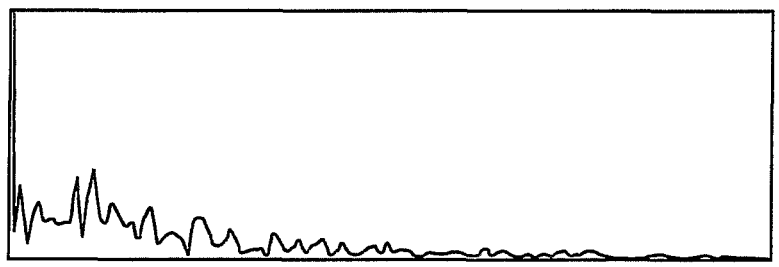
FIG. 6 is the frequency spectrum derived by Fourier analysis for the sinus arrhythmia of FIG. 5.

Referring to FIG. 5 of the drawings, for a patient with abnormal cardiac function (sinus arrhythmia) the plethysmograph obtained in seen to be non-periodic. The frequency spectrum derived by Fourier Analysis for the arrhythmia shown in FIG. 5 is shown in FIG. 6 and it can be seen that the spectrum has a zero frequency component and no harmonics.

Therefore, in accordance with the present invention, the monitor is arranged to compare the frequency spectrum of the detected waveform with the frequency spectrum of an idealised sinus rhythm and to quantify the difference by an index of arrhythmia. The Arrhythmia Index is derived by mathematical analysis as described hereinafter.

An idealised model of the spectrum for sinus rhythm is simulated and stored in the processing unit 11 of the monitor. This simulated spectrum consists of a series of decaying pointed peaks of fixed width separated by a frequency f which is equal to the frequency of the peak of the greatest magnitude. The peaks have a 1/f amplitude and the modelling function have zero value between the peaks. This modelling function $P_{(f)}$ is area normalised and is independent of fundamental frequency in order to allow the frequency to be chosen to match the frequency of the sensed patient plethysmogram.

The monitor is arranged to apply a Fourier transformation to the patient plethysmogram $S_{(f)}$ and to convert the transform to frequency and modulus form. The Fourier transform produces real and imaginary components from which amplitude and phase may be derived. The phase information is discarded and only the amplitude is used in further calculations.

Next, a peak result is obtained by evaluating the following product summation for every value of $P_{(f)}$ between 0.6 and 3.3 hertz (40 to 200 heart beats per minute):

$$\Sigma P_{(f)} S_{(f)} \Delta f \qquad 1.$$

The integrals used in the above calculation are preferably limited to the area of the frequency spectrum from the fundamental frequency to the third or fourth harmonic, since the area outside this range is negligible and does not need to be considered.

Figure 7:
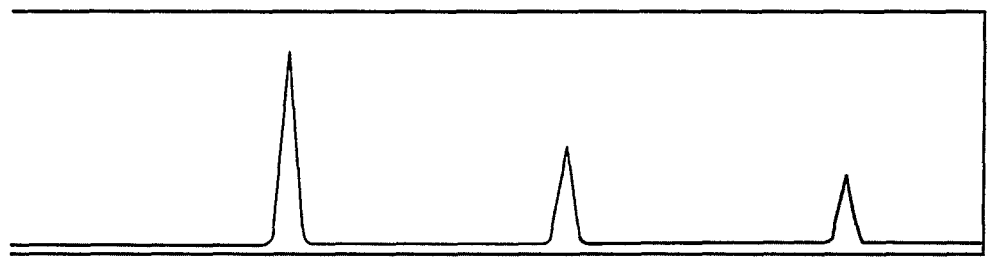
FIG. 7 is the peak function frequency spectrum of an idealised sinus rhythm having a fundamental frequency derived from the sinus arrhythmia of FIG. 5.

The value of the modelling function $P_{(f)}$ that yields the greatest product summation obtained using equation 1 identifies the best match possible between the idealised model of the spectrum for sinus rhythm and the derived spectrum, thereby indicating the heart rate (fundamental component) of the patient. This value of $P_{(f)}$ is known as the peak function and produces the waveform of FIG. 7, where the peak having the greatest magnitude lies at the fundamental frequency of the spectrum.

The magnitude of the greatest product summation obtained using equation 1 can itself be used to provide an indication of whether or not the patient is suffering from atrial fibrillation. However, the sensitivity of this index can be improved by introducing a second function, the trough function $T_{(f)}$, which is derived from the peak function $P_{(f)}$ and ascribes weightings to the areas between the peaks of FIG. 7.

Figure 8:
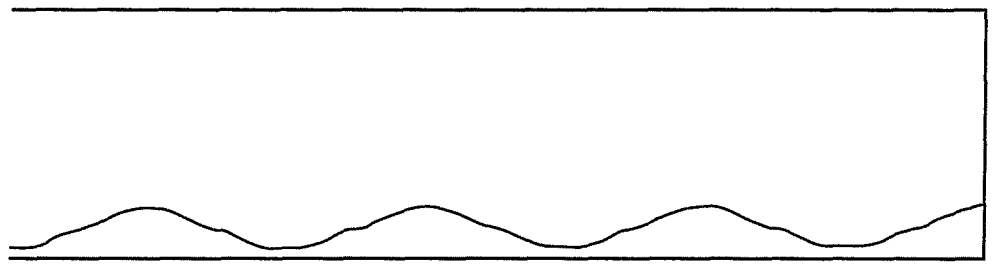
FIG. 8 is the trough function frequency spectrum derived from the peak function of FIG. 7.

Referring to FIG. 8 of the drawings, there is shown the frequency domain waveform of the trough function $T_{(f)}$ having the same fundamental frequency as the derived peak function $P_{(f)}$. This trough function is similarly area normalised.

The Arrhythmia Index is thus obtained as the ratio of the two product integrals:

$$\text{Arrhythmia index} = \frac{\sum T_f S_f \Delta f}{\sum P_f S_f \Delta f}$$

where $T_{(f)}$ and $P_{(f)}$ are the trough and peak functions derived from the spectrum $S_{(f)}$.

The above process will typically yield indices of 0.05 to 0.2 for patients in sinus rhythm and 0.3 and higher for patients with abnormal cardiac rhythm, probably caused by atrial fibrillation. Accordingly, any patients having indices of 0.3 and higher can be referred to a cardiologist for further investigation.

Trials have shown that from the 340 patients that were analysed, there were only 7 False Positives and 0 False Negatives. Accordingly, every person suffering from abnormal cardiac rhythm was correctly identified.

It will be appreciated that whilst a monitor in accordance with the present invention is not able to diagnose atrial fibrillation, the monitor can reliably detect an abnormal heart rhythm, which may have otherwise remained undetected. The monitor can thus be used as a screening tool within the community by relatively unskilled persons and those identified as possibly having an abnormal heart rhythm can be referred for ECG analysis by a cardiologist.

While the preferred embodiments of the invention have been shown and described, it will be understood by those skilled in the art that changes of modifications may be made thereto without departing from the true spirit and scope of the invention.

The invention claimed is:

1. A monitor for monitoring the heart of a patient, the monitor comprising a sensor for producing a first waveform of the patient's actual heart rhythm, a processing unit that is configured to generate first data pertaining to the first waveform of the patient's actual heart rhythm and to store second data pertaining to a second waveform of a simulated ideal heart rhythm that is simulated using an idealized model, said second data representing a peak mathematical function which is independent of fundamental frequency and which comprises a series of decaying pointed peaks of fixed width separated by a frequency, f, which is equal to the frequency of the peak of greatest magnitude, wherein the processing unit processes the first data as well as the second data for the first and second waveforms and produces an output dependent on differences between the first and second waveforms.

2. A monitor as claimed in claim 1, in which the sensor is arranged to produce the first waveform of the patient's actual heart rhythm by sensing the electrical activity of the heart of the patient to produce an electrocardiogram.

3. A monitor as claimed in claim 1, in which the sensor is arranged to produce the first waveform of the patient's actual heart rhythm by sensing the pulsatile flow of blood through a part of the patient's body to produce a plethysmogram.

4. A monitor as claimed in claim 3, in which the sensor comprises a light emitter and a light detector arranged to detect a change in the transmissivity of said part of the patient's body as blood flows therethrough in a pulsatile manner.

5. A monitor as claimed in claim 4, in which the light emitter is arranged to emit light having a wavelength of 500 to 1100 nm.

6. A monitor as claimed in claim 1, in which said processing unit is arranged to compare frequency spectrums of said first and second waveforms.

7. A monitor as claimed in claim 6, in which the second waveform has the same or similar fundamental frequency as the first waveform.

8. A monitor as claimed in claim 6, in which the processing unit is operable to determine the fundamental frequency of the waveform of the patient's actual heart rhythm and to compare the frequency spectrum of the first waveform with the frequency spectrum of the idealized waveform having the same or similar fundamental frequency.

9. A monitor as claimed in claim 1, in which said processing unit is arranged to store a model of the frequency spectrum of said second waveform.

10. A monitor as claimed in claim 1, in which the peak mathematical function is area normalized, such that the area beneath and between frequency limits of interest is 1.

11. A monitor as claimed in claim 1, in which the processing unit is arranged to produce a patient mathematical function representative of the frequency spectrum of said first waveform.

12. A monitor as claimed in claim 11, in which the patient mathematical function is produced using a Fourier transformation of said first waveform.

13. A monitor as claimed in claim 11, in which the patient mathematical function is area normalized, such that the area beneath and between frequency limits of interest is 1.

14. A monitor as claimed in claim 1, in which said processing unit is arranged to determine a fundamental frequency of the first waveform by analyzing summations of products involving frequency spectrum data of said first waveform and the stored peak mathematical function of the second waveform.

15. A monitor as claimed in claim 11, in which the processing unit is arranged to produce a number of peak results for a range of values of a stored peak mathematical function representative of the frequency spectrum of the second waveform, each peak result involving summing products of the patient mathematical function of the first waveform with a respective value of the stored peak mathematical function of the second waveform.

16. A monitor as claimed in claim 15, in which the processing unit is arranged to determine the value of the stored peak mathematical function at which the peak results are maximized in order to determine a fundamental frequency of the first waveform.

17. A monitor as claimed in claim 15, in which peak results are derived by summing products of the patient mathematical function of the first waveform with a respective value of the stored peak mathematical function for a range of frequencies.

18. A monitor as claimed in claim 17, in which the range of frequencies extends between 0.6 and 3.3 hertz.

19. A monitor as claimed in claim 17, in which the range of the frequencies includes a fundamental frequency of the first waveform and at least one harmonic frequency of such fundamental frequency.

20. A monitor as claimed in claim 15, in which the processing unit introduces a trough function comprising a mathematical function representative of the inverse frequency spectrum of said second waveform.

21. A monitor as claimed in claim 20, in which said trough function is area normalized, the processing unit being arranged to produce a trough result by summing products of the produced mathematical function of the first waveform with the trough function at a determined fundamental frequency.

22. A monitor as claimed in claim 21, in which the trough result is divided by the peak result to provide an index of cardiac arrhythmia.

23. A method of examining an output waveform of a sensor arranged to monitor the heart of a patient, the method comprising simulating an ideal heart rhythm using an idealized model and storing second data pertaining to a second waveform of the simulated ideal heart rhythm, said second data representing a peak mathematical function which is independent of fundamental frequency and which comprises a series of decaying pointed peaks of fixed width separated by a frequency, f, which is equal to the frequency of the peak of greatest magnitude, and processing first data pertaining to the output waveform of the sensor as well as the stored second data and producing an output dependent on differences between the output waveform and the second waveform of the simulated ideal heart rhythm.

* * * * *